United States Patent [19]
Ruckenstein et al.

[11] Patent Number: 4,929,510
[45] Date of Patent: May 29, 1990

[54] BIOCOMPATIBLE POLYMER ARTICLES

[75] Inventors: Eli Ruckenstein, Amherst, N.Y.; Dennis B. Chung, Upper Marlboro, Md.

[73] Assignee: State University of New York, Albany, N.Y.

[21] Appl. No.: 187,731

[22] Filed: Apr. 29, 1988

[51] Int. Cl.$^5$ .............................................. B32B 27/30
[52] U.S. Cl. .................................. 428/520; 428/522; 433/201.1; 523/112; 523/113; 523/122; 523/105; 604/16
[58] Field of Search ................. 428/520, 522; 523/112, 523/105, 122, 113; 433/201.1; 604/16

[56] References Cited

U.S. PATENT DOCUMENTS 4,117,035 9/1978 Hillier et al. ...................... 523/112

OTHER PUBLICATIONS

E. Ruckenstein et al., A Surface Energetic Criterion of Blood Compatibility of Foreign Surfaces, Journal of Colloid and Interface Science, vol. 101, No. 2, Oct. 1984.

Primary Examiner—Edith Buffalow
Attorney, Agent, or Firm—Ellen K. Park; Michael L. Dunn

[57] ABSTRACT

A polymer article and a method for making the polymer article. The polymer article includes a hydrophobic polymer substrate and a block copolymer. The block copolymer has at least first and second blocks. The first block is more hydrophobic than the second block. The molecules of the block copolymer are secured into the surface of said substrate by means of the first block and at least a portion of the second block, outwardly extends from the surface of the substrate into the environment.

The method for making the polymer article, comprising a block copolymer and a hydrophobic substrate, comprises the steps of: (a) forming a solution of a block copolymer and a solvent which will solubilize said block copolymer and swell said substrate. The block copolymer has at least a first and second block. The first block is more hydrophobic than the second; (b) treating a hydrophobic substrate with the solution for a sufficient time to swell the substrate surface and enable at least a part of the more hydrophobic block to be deposited on the substrate; (c) removing block copolymer deposited substrate from the solvent; and, (d) placing block copolymer deposited substrate in water for a predetermined time until said block copolymer is oriented such that the more hydrophobic block is entrapped in the substrate and the less hydrophobic block is exposed to water.

15 Claims, 5 Drawing Sheets

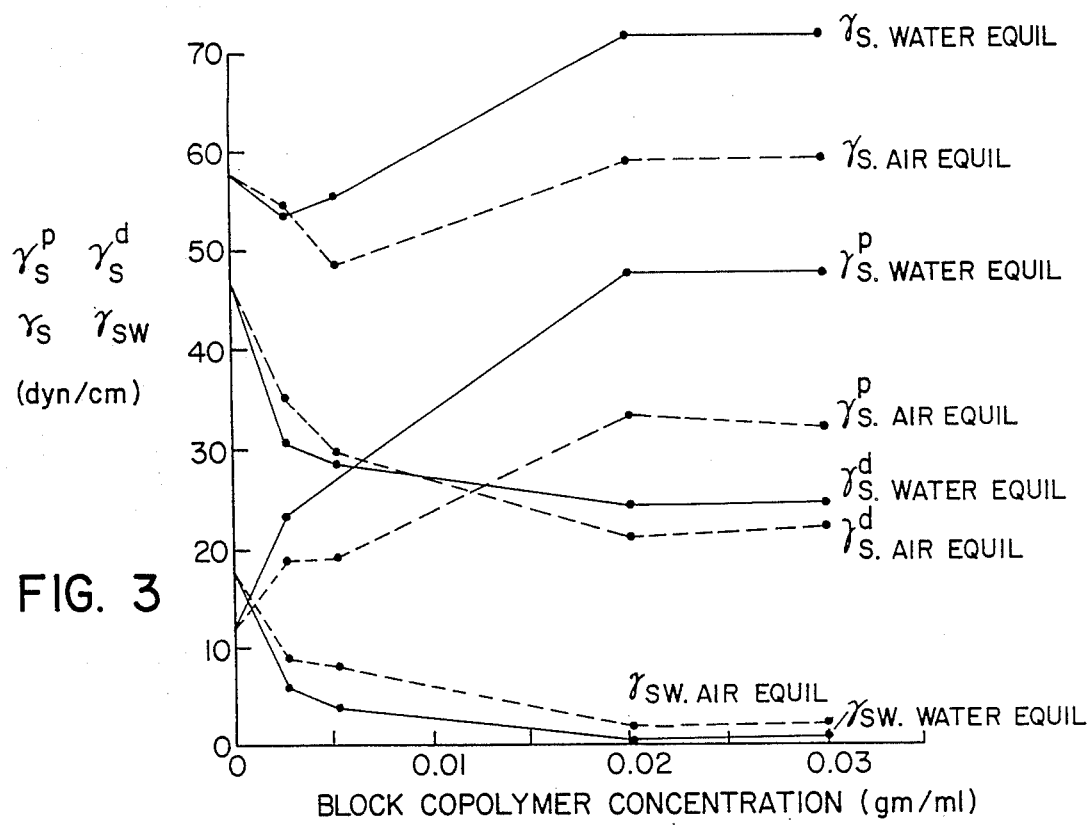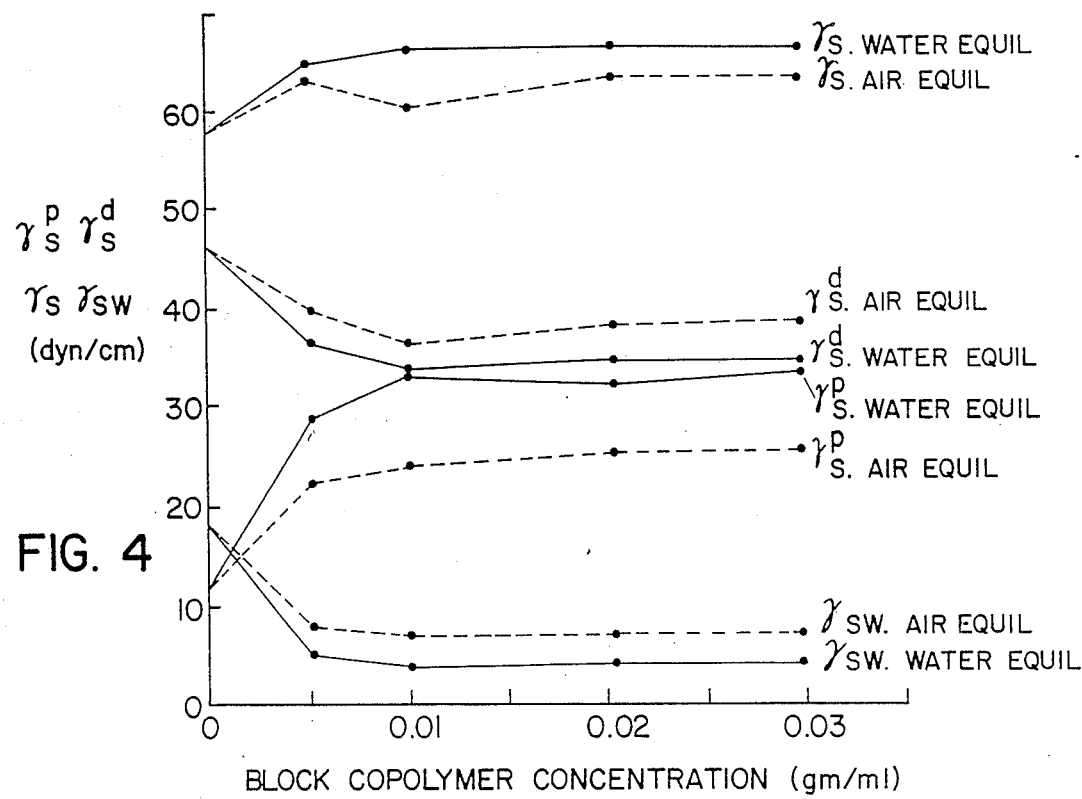

BIOCOMPATIBLE POLYMER ARTICLES

BACKGROUND OF THE INVENTION

The invention relates in general to polymers and more particularly to polymers useful as biomaterials. A practical biomaterial must exhibit two important qualities. First, it must possess suitable mechanical properties. For example, if the biomaterial is to be used as a dental implant, it must be hard and rigid. On the other hand, if it is to be used as a diaphragm of an artificial heart which must flex more than 50 million times per year it must have elastomeric bulk properties and endure cyclic deformation and flexing throughout the life of its host. Second, the biomaterial must have a non-thrombogenic surface. The latter requirement is particularly critical since most biomaterial failures are due to the occurrence of thrombogenic responses at the biomaterial's surface. Several approaches have been attempted in order to identify biocompatible surfaces.

In the past, there have been two main approaches to prepare biocompatible surfaces. The first approach has been to attempt to reduce the thrombogenicity of the surface by coating the material's surface with proteins or hydrogels. The second approach has been the surface treatment by three main methods. The first is the ionic binding of heparin onto the surface. The second is the covalent binding of heparin onto a polymer material and the third method is chemical modification of the polymer surface in order to confer heparin like properties.

Ruckenstein and Gourisankar (Ruckenstein, E., and Gourisankar, S., J. Colloid Interface Sci. 101, 436 (1984)) suggested that the surface properties of a biomaterial must be selected such as to have a very low (preferably zero) interfacial free energy between the solid and the environmental liquid, since under such conditions, the thermodynamic driving force for deposition on the surface is very low. Therefore neither proteins or cellular components will deposit on the surface. A very small interfacial free energy (near zero) is, however, undesirable from the point of view of mechanical stability of the interface. Since the cellular elements of blood are compatible with blood, and their interface with the medium (blood plasma) is also mechanically stable, a blood-biomaterial interfacial tension of about the same magnitude as the cell-medium interfacial tension ($\gamma_{sw} \approx 1-3$ dyn/cm) might provide a foreign surface with long term compatibility as well as mechanical stability of the interface. Assuming that the surface free energies can be written as the sum of a dispersion and polar component and employing the geometric mean for the interaction energy between the two phases, they conclude that the polar components of bioenvironments (biofluids, blood, marine environment, tear environment etc.) and biomaterial should be near to one another and the dispersion components should satisfy the same condition.

SUMMARY OF THE INVENTION

The invention includes polymer articles and a method for making the polymer articles. The polymer article comprises a hydrophobic polymer substrate and block copolymer molecules. The block copolymer molecule has at least first and second blocks. The first block is more hydrophobic than the second block. The molecules of the block copolymer are secured into the surface of said substrate by means of the first block and at least a portion of the second block, outwardly extends from the surface of the substrate into the environment.

The method for making the polymer article, comprising a block copolymer and a hydrophobic substrate, comprises the steps of: (a) forming a solution of a block copolymer and a solvent which will solubilize said block copolymer and swell said substrate. The block copolymer has at least a first and second block. The first block is more hydrophobic than the second; (b) treating a hydrophobic substrate with the solution for a sufficient time to swell the substrate surface and enable at least a part of the more hydrophobic block to be deposited on the substrate; (c) removing block copolymer deposited substrate from the solvent; and, d) placing block copolymer deposited substrate in water for a predetermined time until said block copolymer is oriented such that the more hydrophobic block is entrapped in the substrate and the less hydrophobic block is exposed to water.

Accordingly, an overall object of the invention is to provide a polymer article and a method of making the polymer article. The polymer articles of this invention have an exposed hydrophilic surface to the environment and are biocompatible. In addition, the polymer articles are also mechanically stable.

Other objects of the invention will become more apparent to those skilled in the art from the following detailed description.

It is to be understood that in accordance with the present invention, the hydrophobic/hydrophilic components may be inverted, i.e. a hydrophilic substrate may be used and the hydrophilic block of the copolymer is secured into the hydrophilic substrate. This "inverted" article may be used in a hydrophobic environment wherein the hydrophobic blocks extend outwardly from the substrate.

BRIEF DESCRIPTION OF THE DRAWINGS

FIG. 2 through 10 are graphs of surface free energy components and interfacial free energies against block copolymer concentration for the samples of materials prepared in accordance with the invention.

DETAILED DESCRIPTION OF THE INVENTION

Figure 1A:
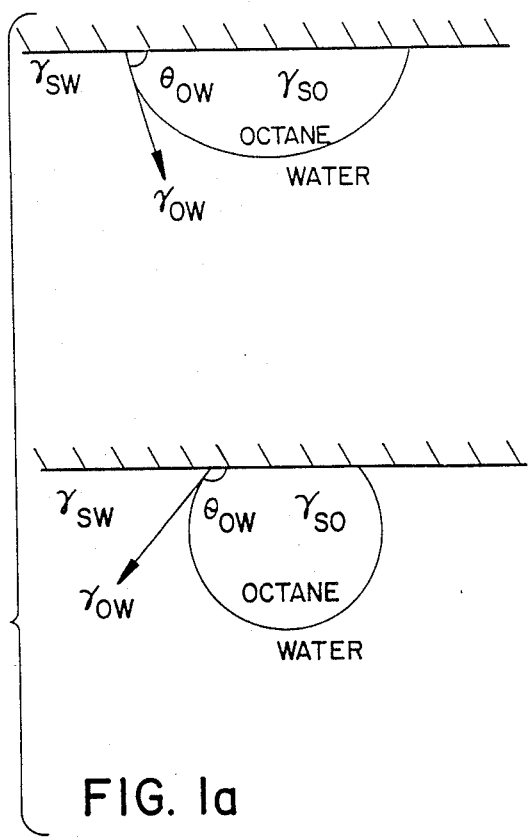
FIG. 1 (a) is an illustration of an inverted octane drop in water. Subscripts so, sw, and ow represents solid-octane, solid-water, and octane-water interfaces, respectively. $\theta_{o/w}$ the octane-in-water contact angle. The more hydrophobic solid surface (above) has a smaller contact angle than the more hydrophilic solid surface (below). (b) Illustration of an inverted air bubble in water. Subscripts sa, sw, and aw represent solid-air, solid-water, and air-water interfaces, respectively. $\theta_{a/w}$ represents the air bubble-in-water contact angle.

The surface modification technique presented here involves the deposition of an A-B block copolymer onto the surface of a hydrophobic polymer.

Polymer as used herein is defined as a macromolecule formed by the union of smaller molecules of the same kind called monomers.

Copolymer as used herein is defined as a polymer containing two or more different monomers.

Block copolymer as used herein is a copolymer whose molecule is made up of sections, each section being formed from a single monomer.

Hydrophobic as used herein is descriptive of having a lack of affinity for water.

Hydrophilic as used herein is descriptive of having an affinity for water.

The hydrophobic polymer substrates used with this invention may be any hydrophobic polymer. Suitable hydrophobic polymers may be but are not limited to thermoplastic polymers and other synthetic polymers, used in the examples hereunder. Examples of suitable substrates which may be used with the present invention are polymethyl methacrylate, polystyrene and polyvinyl acetate. Water will not easily wet the surface of such hydrophobic polymers and will usually form drops on the surface. In general the more hydrophobic the polymer, the greater the contact angle of such a drop with the surface. In general the preferred hydrophobic polymers will have a contact angle greater than the contact angle of a water drop with polyvinyl acetate.

Suitable block copolymers are those that have at least a first and second block within each of the molecules of the block copolymer, where the first block is more hydrophobic than the second block. Examples of such block copolymers may include multibranch copolymers wherein a plurality of hydrophobic blocks and/or a plurality of hydrophilic blocks are present and may also include linear block copolymers wherein more than one block is in the chain. A preferred block copolymer is a diblock copolymer, and most preferably an A-B diblock copolymer where B is more hydrophobic than A and is composed of a relatively hydrophobic chain linearly attached to a more hydrophilic (less hydrophobic) chain.

Every feature of the block copolymer serves a specific purpose. The hydrophobic segment of the block copolymer functions as an anchor. Deposits of short-chained surfactants, such as sodium dodedyl sulfate (SDS) (which has a hydrophobic tail consisting of 12 carbons) and aerosol OT (which has a dual hydrophobic tail consisting of 8 carbons each) demonstrated that surfactants with relatively short hydrophobic chains were not strongly adherent to the polymeric substrate. Therefore the hydrophobic chain of the block copolymer must be long enough to interact more extensively, in the presence of a mutual solvent with the substrate, becoming deeply embedded and highly entangled with the latter.

The hydrophilic block attracts water molecules onto the surface of the solid thus converting an otherwise hydrophobic surface into a more hydrophilic one. The polymeric nature of this polar group also offers some advantages over other molecules with smaller polar groups (such as SDS and aerosol OT). The long hydrophilic chain segment has the capability to respond to various environments through structural rearrangement in order to minimize the interfacial free energy. For example, a polyethylene oxide block of the PEOPO (poly(ethylene oxide-propylene oxide)) block copolymer can acquire a more extended configuration in an aqueous environment in order to accommodate the hydrogen bonding and other polar interactions between itself and the water molecules. In an octane environment, however, it will form a more oil-compatible configuration. Last, in an air environment, the polyethylene oxide chain rearranges in a semicrystalline structure. In short, such polymeric groups can more easily change their structural configuration in order to achieve improved compatibility with the environment.

The deposition of a hydrophilic group onto the surface of a hydrophobic polymer facilitates a reduction of the interfacial tension with water, and this improves the biocompatibility. The hydrophilic polymeric chain also plays, however, another important role. Polyethylene oxide can adopt conformations in which the methylene groups are encaged by a dynamic network of water molecules which, at the same time, are hydrogen bonded to the ether oxygen. This generates steric repulsion which will significantly inhibit the adsorption of blood proteins. A similar behavior will occur with any sufficiently hydrophilic block.

The block copolymers having the above characteristics may be made by any method known to those skilled in the art. In addition, the block copolymers used with this invention may be obtained commercially. Examples of A-B block copolymers which may be utilized are:
poly(ethylene oxide-propylene oxide)
 PEOPO - 3:1, 10,000:3,333 MW (molecular weight)
 Catalog No. 16276
 Polysciences, Inc. Warrington, PA 18976-2590;
poly (N-vinyl-pyrrolidone-vinyl acetate)
 PVPVA - 60/40 copolymer powder
 Scientific Polymer Products, Ontario, NY, and;
poly (N-vinylpyrrolidone-styrene)
 PVPS - 40 % solution in water, 40% N-Vinylpyrrolidone
 Catalog No. 371
 Scientific Polymer Products, Ontario, N.Y.

In addition to the hydrophobic polymer substrates and the block polymers of this invention, the method for making biocompatible polymer articles involves the use of two liquids. The first liquid is a solvent. Suitable solvents for this invention may be any solvent which is capable of solubilizing both the block copolymer and the hydrophobic polymer substrate or any solvent which will solubilize the block copolymer and swell the hydrophobic substrate. Examples of suitable solvents useful for this invention are toluene, benzene, acetone, methanol and chloroform. A suitable second liquid is one which may be utilized for entrapping and orienting the block copolymer on the substrate surface. A preferred second liquid is water. However, other polar media may also be suitable.

The following examples and preparations describe the manner and process of making and using the invention and set forth the best mode contemplated by the inventor of carrying out the invention, but are not to be construed as limiting.

In accordance with the invention, a solution of an A-B block copolymer where B is more hydrophobic than A, is prepared. A hydrophobic polymer of any desired shape and form, for example a sheet of solid polymer cut into ½ by 1-in. pieces may be utilized. A two-liquid method is employed. One of the liquids is a solvent for the block copolymer as well as for the hydrophobic solid, while the second liquid is water. The solid is immersed for a short time into a solution of the block copolymer. After its withdrawal from the solution, the polymer sheet is introduced in water for a predetermined time. Table I hereunder describes a variety of polymer articles made in accordance with this invention.

TABLE I

Sample A: polymethyl methacrylate substrate was immersed into a solution of PEOPO in benzene (0.005 g/ml) for 5 min. then was immediately introduced in water where it was kept for 24 h.

Sample B: polymethyl methacrylate substrate was immersed into a solution of PEOPO in benzene (0.01 g/ml) for 5 min, then was immediately introduced in water where it was kept for 24 hours.

Sample C: Polymethyl methacrylate substrate was immersed into a solution of PEOPO in benzene (0.02 g/ml) for 5 min, then was immediately introduced in water where it was kept for 24 hours.

Sample D: polymethyl methacrylate substrate was immersed into a solution of PEOPO in benzene (0.03 g/ml) for 5 min, then was immediately introduced in water where it was kept for 24 hours.

Samples E, F, G and H correspond to samples A, B, C and D except that the samples were not introduced into water but were air-dried.

Sample I: Polystyrene substrate was immersed into a solution of PVPS in chloroform (0.02 g/ml) for 5 seconds, then was immediately introduced in water where it was kept for 24 h.

Sample J: polymethyl methacrylate substrate was immersed into a solution of PVPS in chloroform (0.02 g/ml) for 5 s, then was immediately introduced in water where it was kept for 24 h.

Sample K: Polystyrene substrate was immersed into a solution of PEOPO in benzene (0.02 g/ml) for 5 s. then was immediately introduced in water where is was kept for 24 h.

Sample L: Polymethyl methacrylate substrate was immersed into a solution of PEOPO in benzene (0.02 g/ml) for 5 min, then was immediately introduced in water where it was kept for 24 h.

Sample M: Polyvinyl acetate substrate was immersed into a solution of PEOPO in benzene (0.02 g/ml) for 5 s, then was immediately introduced in water where it was kept for 24 h.

Sample N: Polystyrene substrate was immersed into a solution of PVPVA in chloroform (0.02 g/ml) for 5 s, then was immediately introduced in water where it was kept for 24 h.

Sample O: Polymethyl methacrylate substrate was immersed into a solution of PVPVA in chloroform (0.02 g/ml) for 5 s, then was immediately introduced in water where it was kept for 24 h.

Sample P: Polyvinyl acetate substrate was immersed into a solution of PVPVA (0.02 g/ml) in chloroform for 5 s, then was immediately introduced in water where it was kept for 24 h.

* The substrate was immersed for a short time in solution when it is highly soluble in the solvent: it was immersed in solution for a longer time when it is not highly soluble in the solvent.

These samples were subjected to standard contact angle measurements known to those skilled in the art. The contact angle technique is employed to evaluate the polar and dispersion components of the surface free energy of the solid and to confirm that the deposited block copolymers are not extracted during long exposures to the aqueous media. Examples of observed contact angles are set forth in Table 1(a).

A detailed description of the relationship of surface free energy components and interfacial free energies to block copolymer concentrations for the materials prepared in accordance with the invention may be found in FIGS. 2-10 as follows. Symbols in the figures are explained later in this detailed description of the invention.

Figure 2:
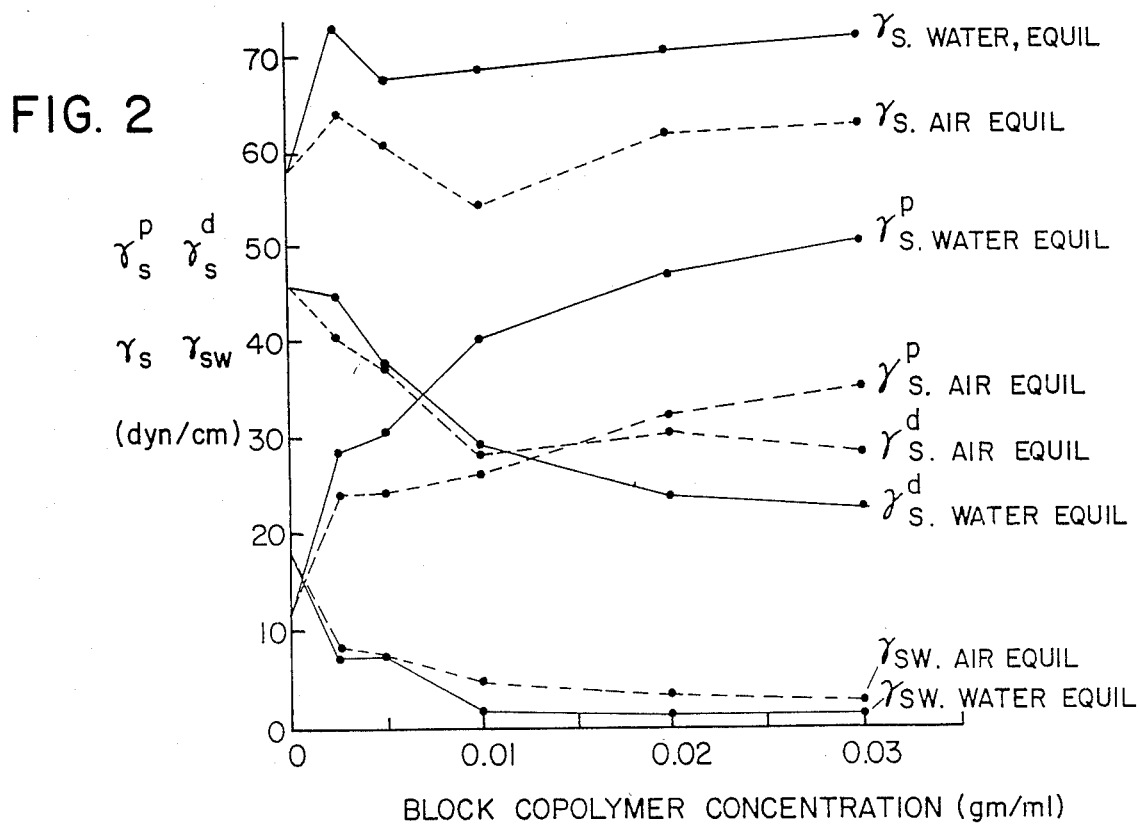

FIG. 2 shows variations in surface free energy components and the solid-water interfacial free energies for polymethyl methacrylate treated with poly(ethylene oxide-propylene oxide) as a function of block copolymer solution concentration. Samples represented by solid lines are prepared by immersing the polymeric substrate into the solution of poly(ethylene oxide-propylene oxide) in benzene for 5 min. then immediately introducing it into water where it is kept for 24 h. Samples represented by dashed lines are prepared by immersing the polymeric substrate into the block copolymer solution for 5 min. then withdrawing the substrate from the solution and allowing it to dry completely in air. The interfacial free energy between the latter samples and water was determined after equilibration in water for 24 h.

FIG. 3 shows variations in surface free energy components and solid-water interfacial free energies for polymethyl methacrylate treated with poly(ethylene oxide-propylene oxide) as a function of block copolymer solution concentration. Samples represented by solid lines are prepared by immersing the polymeric substrate into the solution of poly(ethylene oxide-propylene oxide) in toluene for 1 min. then immediately introducing it into water where it is kept for 24 h. Samples represented by dashed lines are prepared by immersing the polymeric substrate into the block copolymer solution for 5 min. then withdrawing the substrate from the solution and allowing it to dry completely in air. The interfacial free energy between the latter samples and water was determined after equilibration in water for 24 h.

FIG. 4 shows variations in surface free energy components and solid-water interfacial free energies for polymethyl methacrylate treated with poly(ethylene oxide-propylene oxide) as a function of block copolymer solution concentration. Samples represented by solid lines are prepared by immersing the polymeric substrate into the solution of poly(ethylene oxide0-propylene oxide) in acetone for 5 min. then immediately introducing it into water where it is kept for 24 h. Samples represented by dashed lines are prepared by immersing the polymeric substrate into the block copolymer solution for 5 min. then withdrawing the substrate from the solution and allowing it to dry completely in air. The interfacial free energy between the latter samples and water was determined after equilibration in water for 24 h.

Figure 5:
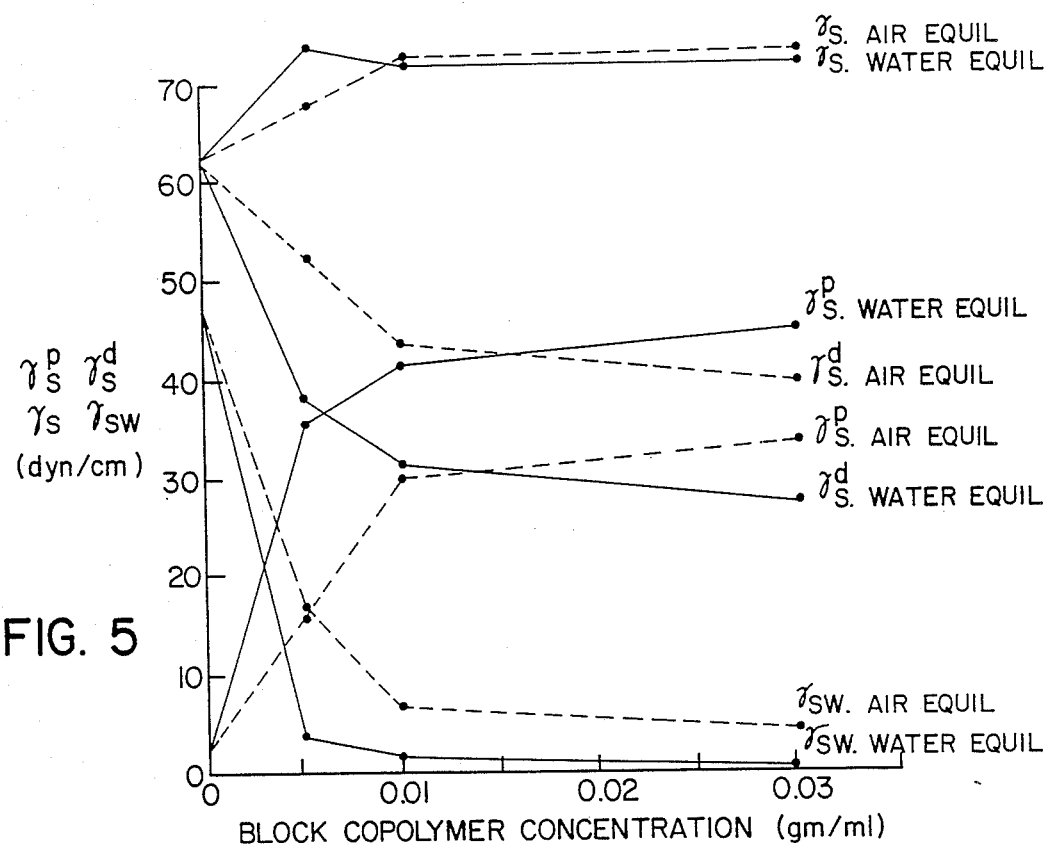

FIG. 5 shows variations in surface free energy components and solid-water interfacial free energies for polystyrene treated with polyvinylpyrrolidone-styrene as a function of block copolymer solution concentration. Samples represented by solid lines are prepared by immersing the polymeric substrate into the solution of polyvinylpyrrolidone-styrene in chloroform for 5 s. then immediately introducing it into water where it is kept for 24 h. Samples represented by dashed lines are prepared by immersing the polymeric substrate into the block copolymer solution for 5 s. then withdrawing the substrate from the solution and allowing it to dry completely in air. The interfacial free energy between the latter samples and water was determined after equilibration in water for 24 h.

Figure 6:
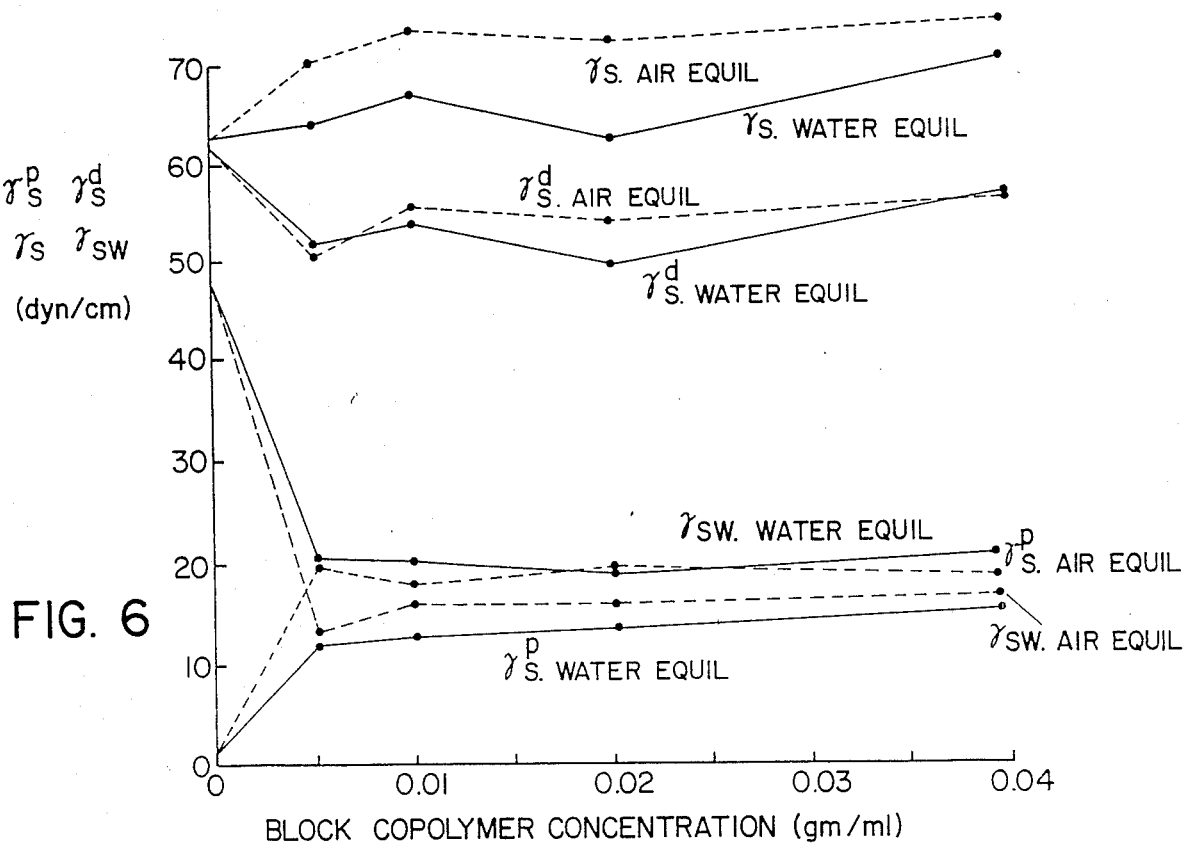

FIG. 6 shows variations in surface free energy components and solid-water interfacial free energies for polystyrene treated with poly(ethylene oxide-propylene oxide) as a function of block copolymer solution concentration. Samples represented by solid lines are prepared by immersing the polymeric substrate into the solution of poly(ethylene oxide-propylene oxide) in benzene for 5 s. then immediately introducing it into water where it is kept for 24 h. Samples represented by dashed lines are prepared by immersing the polymeric substrate into the block copolymer solution for 5 s. then withdrawing the substrate from the solution and allowing it to dry completely in air. The interfacial free energy between the latter samples and water was determined after equilibration in water for 24 h.

Figure 7:
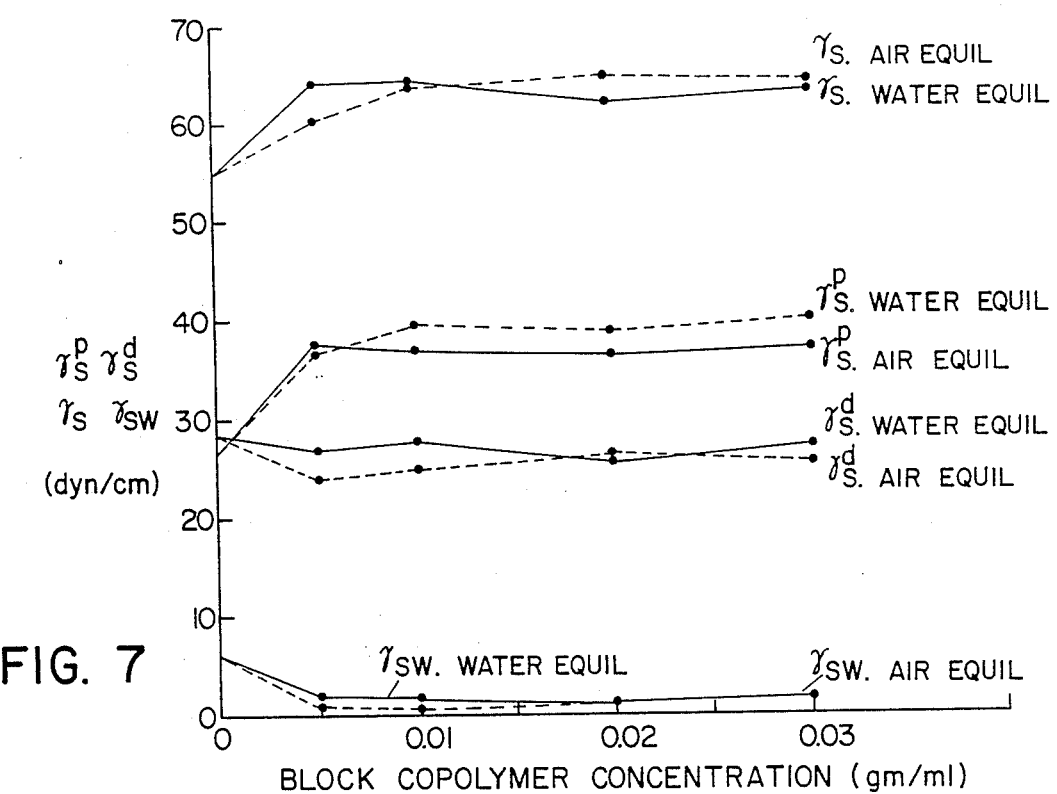

FIG. 7 shows variations in surface free energy components and solid-water interfacial free energies for polyvinyl acetate treated with polyvinylpyrrolidone-styrene as a function of block copolymer solution concentration. Samples represented by solid lines are prepared by immersing the polymeric substrate into the solution of polyvinylpyrrolidone-styrene in chloroform for 5 s. then immediately introducing it into water where it is kept for 24 h. Samples represented by dashed lines are prepared by immersing the polymeric substrate into the block copolymer solution for 5 s. then withdrawing the substrate from the solution and allowing it to dry completely in air. The interfacial free energy between the latter samples and water was determined after equilibration in water for 24 h.

Figure 8:
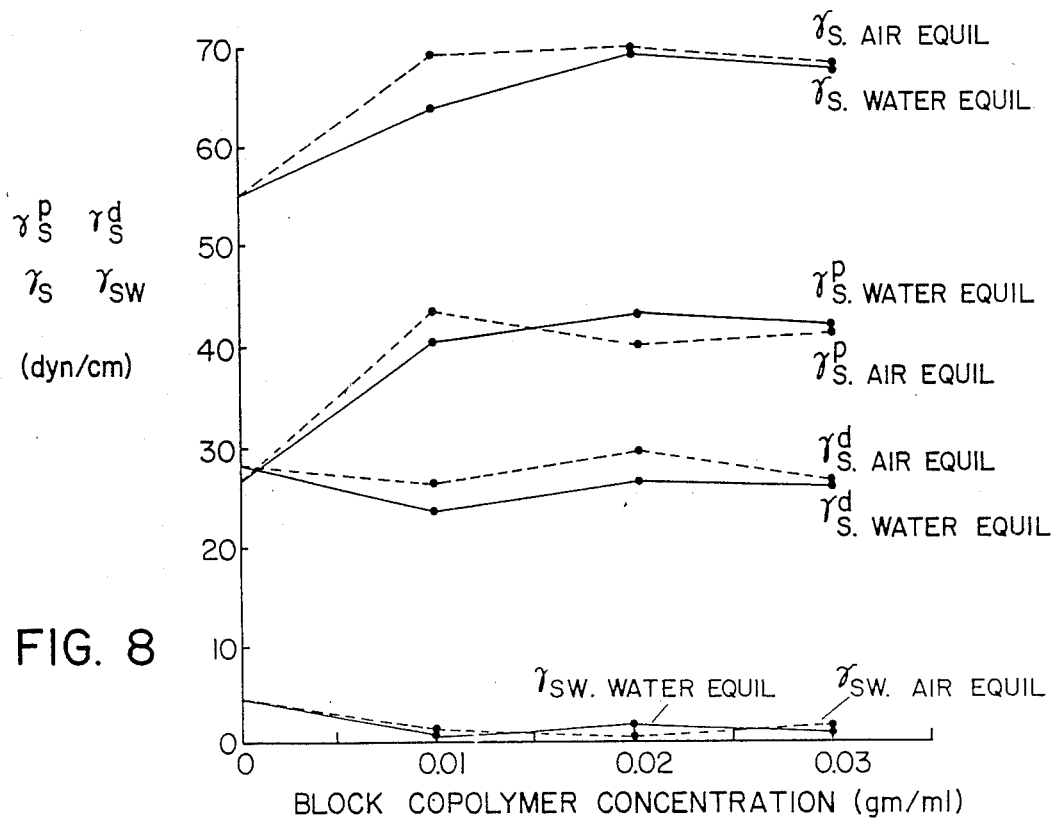

FIG. 8 shows variations in surface free energy components and solid-water interfacial free energies for polyvinyl acetate treated with polyvinylpyrrolidone-vinyl acetate as a function of block copolymer solution concentration. Samples represented by solid lines are prepared by immersing the polymeric substrate into the solution of polyvinylpyrrolidone-vinyl acetate in methanol for 5 s. then immediately introducing it into water where it is kept for 24 h. Samples represented by dashed lines are prepared by immersing the polymeric substrate into the block copolymer solution for 5 s. then withdrawing the substrate from the solution and allowing it to dry completely in air. The interfacial free energy between the latter samples and water was determined after equilibration in water for 24 h.

Figure 9:
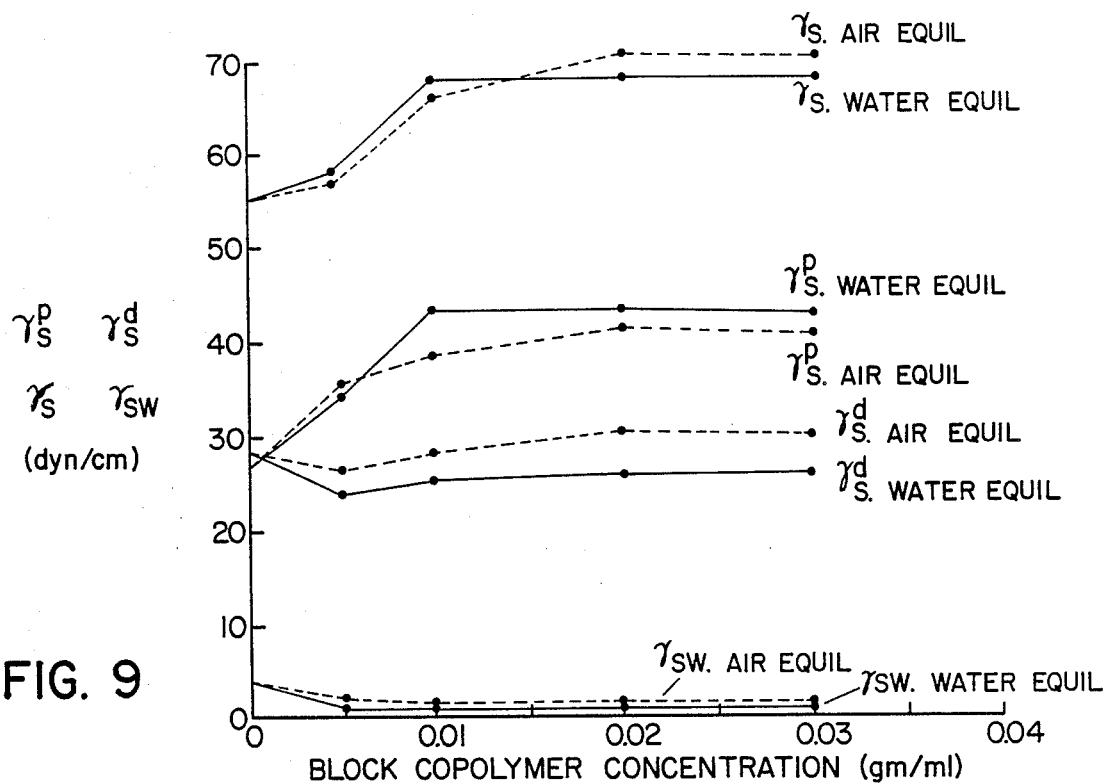

FIG. 9 shows variations in surface free energy components and solid-water interfacial free energies for polyvinyl acetate treated with poly(ethylene oxide-propylene oxide) as a function of block copolymer solution concentration. Samples represented by solid lines are prepared by immersing the polymeric substrate into the solution of poly(ethylene oxide-propylene oxide) in benzene for 5 s. then immediately introducing it into water where it is kept for 24 h. Samples represented by dashed lines are prepared by immersing the polymeric substrate into the block copolymer solution for 5 s. then withdrawing the substrate from the solution and allowing it to dry completely in air. The interfacial free energy between the latter samples and water was determined after equilibration in water for 24 h.

Figure 10:
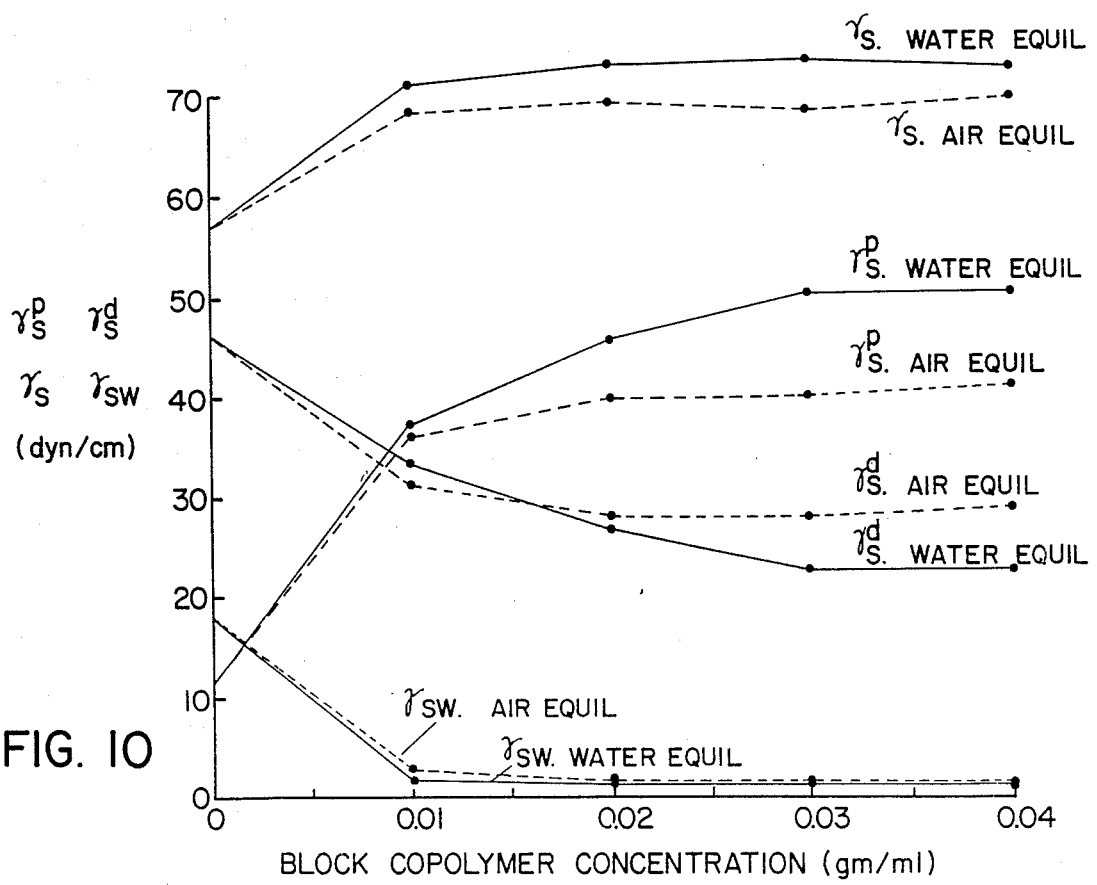

FIG. 10 shows variations in surface free energy components and solid-water interfacial free energies for polymethyl methacrylate treated with polyvinylpyrrolidone-styrene as a function of block copolymer solution concentration. Samples represented by solid lines are prepared by immersing the polymeric substrate into the solution of polyvinylpyrrolidone-styrene in chloroform for 5 s. then immediately introducing it into water where it is kept for 24 h. Samples represented by lines are prepared by immersing the polymeric substrate into the block copolymer solution for 5 s. then withdrawing the substrate from the solution and allowing it to dry completely in air. The interfacial free energy between the latter samples and water was determined after equilibration in water for 24 h.

These results generally indicate that by controlling the amount of block copolymers deposited, it is possible to obtain a surface which will have a low interfacial free energy with a polar medium such as biofluids. Sample K described above results in an interfacial free energy measurement of greater than about 10 dyn/cm between the modified surface and water and therefore is expected to show poor blood compatibility. The biofluid-biomaterial interfacial free energy must be less than about 10 and desirably between about 0.25 and 5 dyn/cm. Most desirably the interfacial free energy should be between about 1 to about 3 dyn/cm.

While not wishing to be bound by theory, it is believed that the advantageous results of the invention are obtained because this technique allows an oriented deposition of the block copolymer such that the hydrophobic block is embedded into the solid while the hydrophilic block remains exposed at the surface to the bioenvironment. The system is kept in water until the polymeric substrate re-solidifies and entraps the entangled more hydrophobic block copolymer. The deposition of the block copolymer increases the polar component of the solid's surface free energy and decreases the dispersion component. As a result, the interfacial free energy between the surface modified polymer and the biofluid will be decreased.

An ideal biocompatible material should have a surface free energy that will be similar to that of water and have a polar component similar to that of water. The interfacial tension between the solid and the aqueous medium (the bioenvironment) should be minimal. The contact angle measurements indicate that by depositing a block copolymer in accordance with this invention, the biocompatibility of the surface of a hydrophobic substrate could be enhanced through reduction of the solid-liquid interfacial free energy, and through the additional inhibition of protein adsorption by the steric repulsion created by the polymeric chains.

Therefore, by selecting the appropriate polymeric material with the desired bulk properties, and modifying its surface property through controlled deposition of block copolymers, it is possible to tailor the properties of the material according to the bulk and interfacial requirements necessary for its application.

For most biomaterials their application involves continuous and prolonged contact with aqueous media. Therefore, successful performance demands stability against extraction of the adsorbed molecules (block copolymers in this case). A simple approach, based on wetting angle measurements was employed to study the extent of extraction of the block copolymer.

As indicated in Table Ia. 16 surfaces treated with various block copolymers (Table Ib details the surface modification procedure) were water-equilibrated for 24 h and then the initial octane-in-water and air bubble-in-water contact angles were measured. The entire system was then kept undisturbed in that environment for 7 days, after which the contact angles of the original probe fluids were measured once again. It was found that the contact angle has decreased for all systems (Table Ia) over the 7-day period.

TABLE I(a)

| Sample | Initial θ and γ of the first probe fluids | | | | Contact angles of first probe fluids after 7 days | | Initial θ and γ of second probe fluids | | | |
|---|---|---|---|---|---|---|---|---|---|---|
| | $\theta_{o/w}$ | $\theta_{a/w}$ | $\gamma_s^p$ | $\gamma_s^d$ | $\theta_{o/w}$ | $\theta_{a/w}$ | $\theta_{o/w}$ | $\theta_{a/w}$ | $\gamma_s^p$ | $\gamma_s^d$ |
| A | 121 | 151 | 29.1 | 40.1 | 109 | 122 | 120 | 153 | 28.6 | 42.8 |
| B | 142 | 156 | 40.8 | 26.3 | 121 | 134 | 142 | 157 | 40.8 | 26.8 |
| C | 151 | 162 | 44.2 | 25.2 | 140 | 147 | 150 | 161 | 44.1 | 25.4 |
| D | 162 | 170 | 48.4 | 26.3 | 138 | 143 | 162 | 170 | 48.4 | 26.3 |
| E | 111 | 142 | 24.5 | 40.3 | 98 | 118 | 110 | 143 | 23.2 | 43.9 |
| F | 115 | 145 | 26.4 | 39.7 | 102 | 123 | 114 | 145 | 25.4 | 41.6 |
| G | 122 | 147 | 29.7 | 35.7 | 108 | 126 | 122 | 147 | 29.7 | 35.7 |
| H | 140 | 156 | 39.6 | 27.8 | 114 | 131 | 140 | 155 | 39.6 | 27.9 |
| I | 118 | 149 | 27.7 | 41.0 | 90 | 106 | 143 | 156 | 40.8 | 26.3 |
| J | 154 | 160 | 45.8 | 22.6 | 130 | 148 | 156 | 166 | 46.4 | 24.2 |
| K | 93 | 122 | 14.0 | 48.2 | 91 | 121 | 95 | 134 | 14.9 | 53.0 |
| L | 145 | 166 | 41.6 | 29.9 | 143 | 141 | 147 | 167 | 42.7 | 28.9 |
| M | 131 | 142 | 34.6 | 24.2 | 130 | 128 | 137 | 153 | 38.2 | 32.4 |
| N | 131 | 145 | 34.6 | 26.7 | 98 | 134 | 132 | 157 | 35.3 | 34.4 |
| O | 135 | 151 | 36.9 | 28.1 | 131 | 138 | 137 | 161 | 38.2 | 32.4 |
| P | 133 | 145 | 35.6 | 25.4 | 128 | 129 | 137 | 149 | 38.2 | 25.0 |

Note:
The first probe fluids have been placed on the water-equilibrated sample at the time considered zero: the second probe fluids have been placed on the same sample 7 days later.

The decrease in contact angle may be due to any combination of the following possible phenomena:

(i) When the octane drop or air bubble comes in contact with the water-equilibrated solid surface, the newly formed interface is thermodynamically unstable and undergoes structural rearrangement toward a more favorable thermodynamic state of reduced interfacial free energy. This surface restructuring tends to expose hydrophobic moieties to a hydrophobic environment and hydrophilic moieties to a hydrophilic one (10–14). As a result, the octane-solid interfacial free energy is reduced, resulting in the decreases of the contact angle.

(ii) As indicated in FIGS. 2–10, the greater the surface concentration of the polar chains, the smaller the interfacial free energy between the surface and water. Therefore, if hydrophilic chains are extracted from the solid surface by the water molecules, the interfacial free energy at the solid-water interface will increase. As a result the contact angle will decrease.

(iii) The block copolymers are surface active and can be therefore adsorbed on the octane-water (or air-water) interface resulting in a reduction of the octane-water (or air-water) interfacial free energy and hence in a decrease of the contact angle.

The effect of aging can be monitored by placing new probe fluids onto the same surface near the original probe fluids. As tabulated in Table Ia, the initial contact angles of the new probe fluids are nearly identical to the initial contact angles of the probe fluids placed 7 days earlier. The obvious implication is that the water-solid interfacial free energy has remained the same throughout the 7-day period of exposure to the aqueous environment and hence that no extraction of the block copolymers has occurred. It also becomes clear that the structural rearrangement of the solid surface at the solid-octane or solid-air interface is responsible for the decrease of the contact angle during the 7-day period.

Of course, the above conclusions imply that the two fluid phases themselves are free of surface active impurities. While precautions have been taken, this possibility should not be excluded.

On can, therefore, speculate that, initially, the polar polymeric chains at the surface were extended into the aqueous phase, but upon contact with the nonpolar probe fluid, they rearranged, exposing more nonpolar surface moieties to the probe fluid. At the same time, the surface regions in contact with water remained unchanged. Hence, the hydrophobic segment of the block copolymer firmly anchors the molecule onto the surface of the substrate. If extraction would have occurred, the polar component of the solid's surface free energy would have decreased. However, this never occurred. In fact, for some systems, the polar component of the solid's surface free energy even increased slightly during the 7-day period of exposure to water. This suggests that some hydrophilic segments of the block copolymer have freed themselves from their entanglement with the hydrophobic molecules of the substrate (or of the block copolymer) and became exposed to the aqueous medium, while concurrently, some hydrophobic moieties "turned away" from the aqueous medium and buried themselves into the hydrophobic bulk.

In Table II, it is shown for four surfaces that they remain stable even after 4 weeks of exposure to water. The increases in the wetting angles are most likely due to surface restructuring and not to the adsorption of the block copolymer molecules.

TABLE Ib

| Sample | Initial θ and γ of the first probe fluids | | | | Contact angles of first probe fluids after 4 weeks | | Initial θ and γ of second probe fluids | | | |
|---|---|---|---|---|---|---|---|---|---|---|
| | $\theta_{o/w}$ | $\theta_{a/w}$ | $\gamma_s^p$ | $\gamma_s^d$ | $\theta_{o/w}$ | $\theta_{a/w}$ | $\theta_{o/w}$ | $\theta_{a/w}$ | $\gamma_s^p$ | $\gamma_s^d$ |
| I | 118 | 149 | 27.7 | 41.0 | 90 | —$^a$ | 148 | 158 | 43.4 | 24.3 |
| K | 93 | 122 | 14.0 | 48.2 | 81 | —$^a$ | 101 | 139 | 18.0 | 51.3 |
| M | 131 | 142 | 34.6 | 24.2 | 130 | —$^a$ | 142 | 155 | 40.6 | 25.9 |

TABLE Ib-continued

| | Initial $\theta$ and $\gamma$ of the first probe fluids | | | | Contact angles of first probe fluids after 4 weeks | | Initial $\theta$ and $\gamma$ of second probe fluids | | | |
|---|---|---|---|---|---|---|---|---|---|---|
| Sample | $\theta_{o/w}$ | $\theta_{a/w}$ | $\gamma_s^p$ | $\gamma_s^d$ | $\theta_{o/w}$ | $\theta_{a/w}$ | $\theta_{o/w}$ | $\theta_{a/w}$ | $\gamma_s^p$ | $\gamma_s^d$ |
| N | 131 | 145 | 34.6 | 26.7 | 97 | —$^a$ | 136 | 157 | 37.5 | 31.2 |

Note
The first probe fluids have been placed on the water-equilibrated sample at the time considered zero; the second probe fluids have been placed on the same sample 4 weeks later.
$^a$The air bubble disappeared during the 4-week period.

The contact angle measurements were performed with a NRL contact angle goneometer (Rame Hart Inc. A-100, Mountain Lakes, N.J.) and its accessories. The 99.99% pure octane was purchased from Aldridge Chemical Co. The water used for the contact angle measurements was doubly deionized and distilled. The accuracy of the contact angle measurements was ±2°.

The solid's surface free energy components were determined from contact angle measurements by using octane and air as probe fluids. FIG. 1a is an illustration of a drop of octane placed in contact with the surface of a water equilibrated solid. Since the reorientation of the polymer molecules beneath the probe fluid is in general a slow process, and the wetting equilibrium is achieved quickly, the "initial wetting angle" measured after a short time (3 min) is considered as the equilibrium wetting angle for the initial structure of the surface.

The surface free energy at the solid-water interface ($\gamma_{sw}$) can be expressed as $$\gamma_{sw} = \gamma_s + \gamma_w - W_{sw}, \qquad [1]$$

where $W_{sw}$ is the work of adhesion between the solid surface and water, and $\gamma_s$ and $\gamma_w$ are the surface free energies of the solid and water, respectively.

The surface free energy of the solid surface is frequently written as the sum of dispersion and polar ($\gamma_s^d$) and polar ($\gamma_s^p$) components. In addition, it is assumed that the dispersion component of the work of adhesion is given by the geometric mean, $$W_{sw}^d = 2(\gamma_s^d \gamma_w^d)^{\frac{1}{2}}, \qquad [2]$$

where $\gamma_w^d$ is the dispersion component of the surface tension of water.

It has been suggested that the use of a geometric mean for the polar component of the work of adhesion as well, i.e., $W_{sw}^p = 2(\gamma_s^p \gamma_w^p)^{\frac{1}{2}}$, where $\gamma_w^p$ is the polar component of the surface tension of water. However, while the geometric mean approximation is acceptable for the dispersion interactions, its validity for polar interactions, particularly when strong hydrogen bonding is involved, is questionable. In addition, the specific acid-base interactions are ignored in the above treatment.

With these approximations, the expression for the solid/water interfacial free energy [2] becomes $$\begin{aligned}\gamma_{sw} &= \gamma_s + \gamma_w - 2(\gamma_s^d \gamma_w^d)^{\frac{1}{2}} - 2(\gamma_s^p \gamma_w^p)^{\frac{1}{2}} \\ &= [(\gamma_s^d)^{\frac{1}{2}} - (\gamma_w^d)^{\frac{1}{2}}]^2 + [(\gamma_s^p)^{\frac{1}{2}} - (\gamma_w^p)^{\frac{1}{2}}]^2.\end{aligned} \qquad [3]$$

Similar approximations can be applied to $\gamma_{ow}$ and $\gamma_{so}$.

Combining the above expressions with Young's equation, one obtains $$\gamma_s^p = (\gamma_w - \gamma_o - \gamma_{ow} \cos\theta_{o/w})^2/4\gamma_w^p. \qquad [4]$$

where $\theta_{o/w}$ is the octane drop's initial contact angle (FIG. 1a).

Figure 1B:
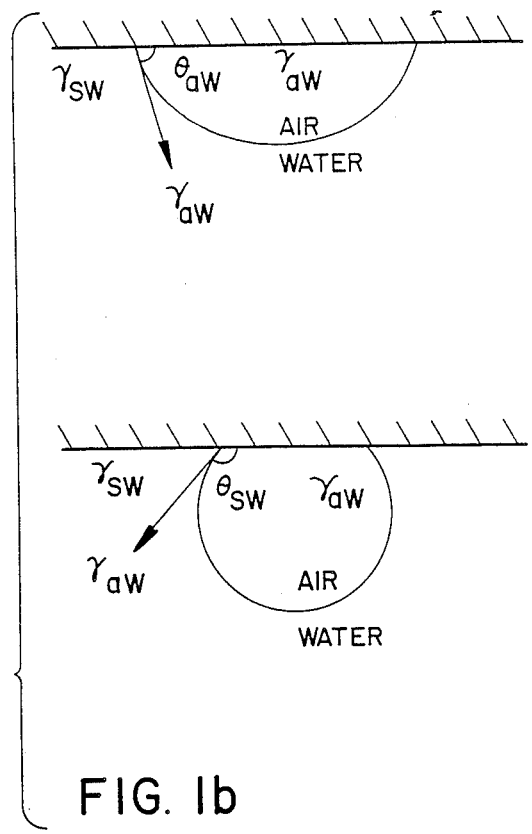

Repeating the same procedure for the inverted air bubble in water (FIG. 1b), one obtains the following expression for the dispersion component of the solid's surface free energy.

$$\gamma_s^d 32 \,[\gamma_w - \gamma_w \cos\theta_{A/w} - 2(\gamma_s^p \gamma_w^p)^{\frac{1}{2}}]^2/4\gamma_w^d, \qquad [5]$$

where $\theta_{A/w}$ is the initial wetting angle of the air bubble in water.

It should be noted that only the initial contact angles should be used in the surface free energy calculations Indeed, the derivation of Eqs. [4] and [5] implies that the solid surface exposed to octane or air is identical to the surface in contact with water, i.e., that the solid undergoes negligible surface restructuring at the solid-octane interface prior to the contact angle measurement. If restructuring does occur at the solid-octane interface prior to the contact angle measurement, then the solid beneath oil or air will have different surface free energy components than the solid beneath water, and Eqs. [4] and [5] will no longer be valid.

The reduction of the interfacial free energy between solid and liquid to low values constitutes the criterion for the design of blood-compatible surfaces. The decomposition of the surface free energies into additive polar and dispersion components, the geometric mean employed for the work of adhesion, and the neglect of specific interactions cast uncertainty on the basic Eqs. [4] and [5]. In addition, the uncertainty is compounded by (a) the possible increase in surface roughness during block copolymer deposition, and (b) the need to measure the initial wetting angle in order to avoid the restructuring of the surface. Obviously, a more satisfactory characterization of the surface is necessary. Ultimately, tests for protein adsorption and platelet deposition should be performed to evaluate the compatibility of the surface.

FIG. 2 shows that as the concentration of polyethylene oxide-propylene oxide in benzene increases, the polar component of the surface free energy also rises. This rise is accompanied by the decrease in the dispersion component. For example, at a concentration of 0.03 g PEOPO/ml benzene the polar component of the surface free energy increases from 11.8 dyn/cm in the untreated state to 49.7 dyn/cm in the treated state (indicated by the solid line labeled $\gamma_s^p$, water equil.) . Conversely, the dispersion component of the surface free energy decreases from an initial value of 45.8 dyn/cm to the final value of 21.8 dyn/cm (indicated by the solid line labeled $\gamma_s^d$, water equil.). As a result the total surface free energy increases from 57.6 to 71.5 dyn/cm (indicated by the solid line labeled $\gamma_s$, water equil.). The solid's interfacial free energy with water ($\gamma_{sw}$, water equil.) was reduced from an initial value of 17.7 dyn/cm to values near zero at high block copolymer concentrations. Inspection of the dashed curves shows that changes in both polar and dispersion components as well as in the total surface free energy are less dramatic than the changes shown by the solid curves. This is accountable in terms of the surface modification technique employed. The samples represented by the dashed curves underwent the benzene solution treatment but did not undergo the critical water treatment step.

Compared to FIG. 2, in FIG. 3 only the benzene was replaced by toluene. The resulting curves show a behavior similar to that of FIG. 2 but reach saturation at a lower concentration of PEOPO. FIG. 4 presents results for PMMA samples treated by using acetone as solvent. Similar to FIGS. 2 and 3, the curves show an increase of the polar component of the surface free energy and a decrease of the dispersion component with increasing PEOPO concentration. However, these curves reach saturation at a lower concentration, of approximately 0.01 g PEOPO/ml acetone and the interfacial free energy $\gamma_{sw}$ at saturation is larger.

FIG. 5 presents the surface free energy components for polystyrene treated with PVPS dissolved in chloroform. The samples which subsequently underwent water treatment (represented by the solid curves labeled $\gamma_s$, water equil.) show a dramatic increase in the polar surface free energy and a dramatic decrease in the dispersion component at a lower block copolymer concentration (between zero and 0.01 g PVPS/ml chloroform). The saturation values of $\gamma_{sw}$ are within 1–3 dyn/cm. Similar to the other specimens mentioned thus far, the air-equilibrated samples (represented by the dashed curves labeled $\gamma_s$, air equil.) exhibit weaker changes in both the dispersion and polar surface free energy components.

When PEOPO was adsorbed instead (FIG. 6), weaker changes in the surface properties occurred with increasing block copolymer concentration. The polar surface free energy component of the water-equilibrated samples never exceeded 15 dyn/cm. Similarly, the dispersion component underwent only a relatively small decline. As a result, the solid-liquid interfacial tension ($\gamma_{sw}$) remained relatively high. An interesting result, which is opposite to those observed with the previous systems, is that the polar surface free energy component of the air-dried samples was greater than that of the water-treated samples. One plausible explanation is that the highly hydrophobic polystyrene molecule is at least partly incompatible with the hydrophobic block of the PEOPO molecule (since the propylene-oxide contains a polar constituent): therefore, in a water environment, the PEOPO molecule will be more easily liberated from its entanglement with the polystyrene molecules. This surface is expected to show poor blood compatibility.

FIGS. 7, 8, and 9 involve the polyvinyl acetate polymer treated with a solution of PVPS in chloroform, a solution of PVPVA in methanol, and PEOPO in benzene, respectively. The polar component of the surface free energy of the solid increases by about 10 dyn/cm and becomes saturated at a relatively low block copolymer concentration; the dispersion component of the surface free energy undergoes a small decline. In addition, there is no marked difference between the water- and air-treated samples. The surface free energy component of polyvinyl acetate seems to be almost insensitive to the solvent and block copolymer employed. This occurs because polyvinyl acetate has a relatively high polar surface free energy compared to the other hydrophobic substrates, and the deposition of block copolymers results in only a modest increase in the polar surface free energy.

FIG. 10 presents the changes in the surface free energy components for PMMA treated with PVPS in chloroform.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A polymer article comprising
   (a) a hydrophobic polymer substrate having a substrate surface; and
   (b) a block copolymer having at least first and second blocks within each of the molecules of the block copolymer, the first block being more hydrophobic than the second block, the molecules of said block copolymer being secured into the surface of said substrate by means of the first block and at least a portion of the second block outwardly extending from the surface.

2. The polymer article of claim 1 wherein said hydrophobic polymer is a member selected from the group consisting of polymethyl methacrylate, polystyrene and polyvinyl acetate.

3. The polymer article of claim 1 wherein said block copolymer is an A-B diblock copolymer where B is more hydrophobic than A.

4. The polymer article of claim 2 wherein said block copolymer is an A-B diblock copolymer where B is more hydrophobic than A.

5. The polymer article of claim 3 wherein said block copolymer is a member selected from the group consisting of poly(ethylene oxide-propylene oxide), poly(N-vinyl-pyrrolidone-vinyl acetate) and poly(N-vinyl-pyrrolidone-styrene).

6. The polymer article of claim 4 wherein said block copolymer is a member selected from the group consisting of poly(ethylene oxide-propylene oxide), poly(N-vinyl-pyrrolidone-vinyl acetate) and poly(N-vinyl-pyrrolidone-styrene).

7. The polymer article of claim 1 wherein interfacial free energy between the polymer article and a bioenvironment is less than about 10 dyn/cm.

8. The polymer article of claim 1 wherein interfacial free energy between the polymer article and water is less than about 10 dyn/cm.

9. The polymer article of claim 1 wherein interfacial free energy between the polymer article and a bioenvironment is between about 0.25 and 5 dyn/cm.

10. The polymer article of claim 1 wherein interfacial free energy between the polymer article and water is between about 0.25 and 5 dyn/cm.

11. The polymer article of claim 1 wherein interfacial free energy between the polymer article and a bioenvironment is between about 1 to 3 dyn/cm.

12. The polymer article of claim 1 wherein interfacial free energy between the polymer article and water is between about 1 to 3 dyn/cm.

13. The polymer article of claim 1 wherein the polymer article is biocompatible.

14. The polymer article of claim 6 wherein the polymer article is biocompatible.

15. A polymer article comprising
(a) a hydrophilic polymer substrate having a substrate surface; and
(b) a block copolymer having at least first and second blocks within each of the molecules of the block copolymer, the first block being more hydrophilic than the second block, the molecules of said block copolymer being secured into the surface of said substrate by means of the first block and at least a portion of the second block outwardly extending from the surface.

* * * * *